US00PP33633P2

(12) United States Plant Patent
Randag

(10) Patent No.: US PP33,633 P2
(45) Date of Patent: Nov. 9, 2021

(54) CALLA LILY PLANT NAMED 'DOZANCORV'

(50) Latin Name: *Zantedeschia sprengeri*
Varietal Denomination: Dozancorv

(71) Applicant: Dümmen Group B.V., De Lier (NL)

(72) Inventor: Cecilius Jan-Jochem Randag, Koedijk (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/313,093

(22) Filed: May 6, 2021

(51) Int. Cl.
*A01H 5/02* (2018.01)
*A01H 6/10* (2018.01)

(52) U.S. Cl.
USPC ..... Plt./490
CPC ..... *A01H 6/10* (2018.05)

(58) Field of Classification Search
USPC ..... Plt./490
CPC ..... A01H 6/10
See application file for complete search history.

(56) References Cited

PUBLICATIONS

UPOV hit on a calla plant named, 'Dozancorv', QZ PBR 20202098, filed Sep. 4, 2020.*

* cited by examiner

*Primary Examiner* — Anne Marie Grunberg
(74) *Attorney, Agent, or Firm* — The Webb law Firm

(57) ABSTRACT

'Dozancorv' is a new variety of calla lily plant having red colored spathes without a throat spot that produces 7-10 inflorescences per approximately 20 cm tuber. The flower stems are about 40-48 cm in height. The leaves are brownish green with maculations present and a smooth texture.

2 Drawing Sheets

Botanical classification: *Zantedeschia sprengeri.*
Varietal denomination: 'Dozancorv'.

BACKGROUND OF THE NEW PLANT

The present invention comprises a new and distinct variety of calla lily, botanically known as *Zantedeschia sprengeri* and hereinafter referred to by the varietal name 'Dozancorv'. 'Dozancorv' is a product of a planned breeding program, which had the objective of creating *Zantedeschia* hybrids for pot flower production in a wide range of colors with a classic flower shape. The new cultivar is a seedling selected from the crossing of *Zantedeschia sprengeri* variety 'Mercedes' (female parent, unpatented) with *Zantedeschia sprengeri* seedling Z981074-4106 (male parent, unpatented). 'Dozancorv' was selected in 2012 by the inventor in 't Zand, The Netherlands as one flowering plant within the progeny of the stated cross.

The first act of asexual reproduction of 'Dozancorv' by tissue culture was performed by the inventor in November of 2015 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants at approximately 8 weeks from unpotted planting in soil in 't Zand, The Netherlands under greenhouse conditions, which approximate those generally used in horticultural practice. Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Dozancorv' which, in combination, distinguish this calla lily as a new and distinct cultivar:

1. Medium red colored spathes without a throat spot;
2. Brownish green colored leaves; and
3. Medium leaf maculations present.

The new variety is similar to its female parent in the following traits: absence of a spathe throat spot, lanceolate leaf shape, yellow spadix color, and green stem color. However, 'Dozancorv' exhibits fewer inflorescences, a stronger flower curve, a shorter spadix length, and stronger stems than its female parent. Further, its female parent exhibits an orange spathe color and light green colored leaves. The new variety is similar to its male parent in the following traits: red spathe color, lanceolate leaf shape, and the presence of leaf maculations. However, 'Dozancorv' exhibits a narrower spathe width, shorter spathe length, and stronger flower curve than its male parent. Further, its male parent exhibits a spathe throat spot, yellow/red spadix color, and red/green stem color.

When compared to calla lily plant named 'Bloody Mary' (U.S. Plant Pat. No. 30,417), both varieties exhibit red colored spathes, but 'Bloody Mary' exhibits secondary spathe colors of yellow and orange/red. Further, the new variety exhibits more leaves than 'Bloody Mary'.

BRIEF DESCRIPTION OF THE DRAWINGS

The accompanying photographic drawings illustrate the new variety taken at approximately 8 weeks of age, with the colors being as nearly true as is possible with color illustrations of this type.

DESCRIPTION OF THE NEW PLANT

Figure 1:
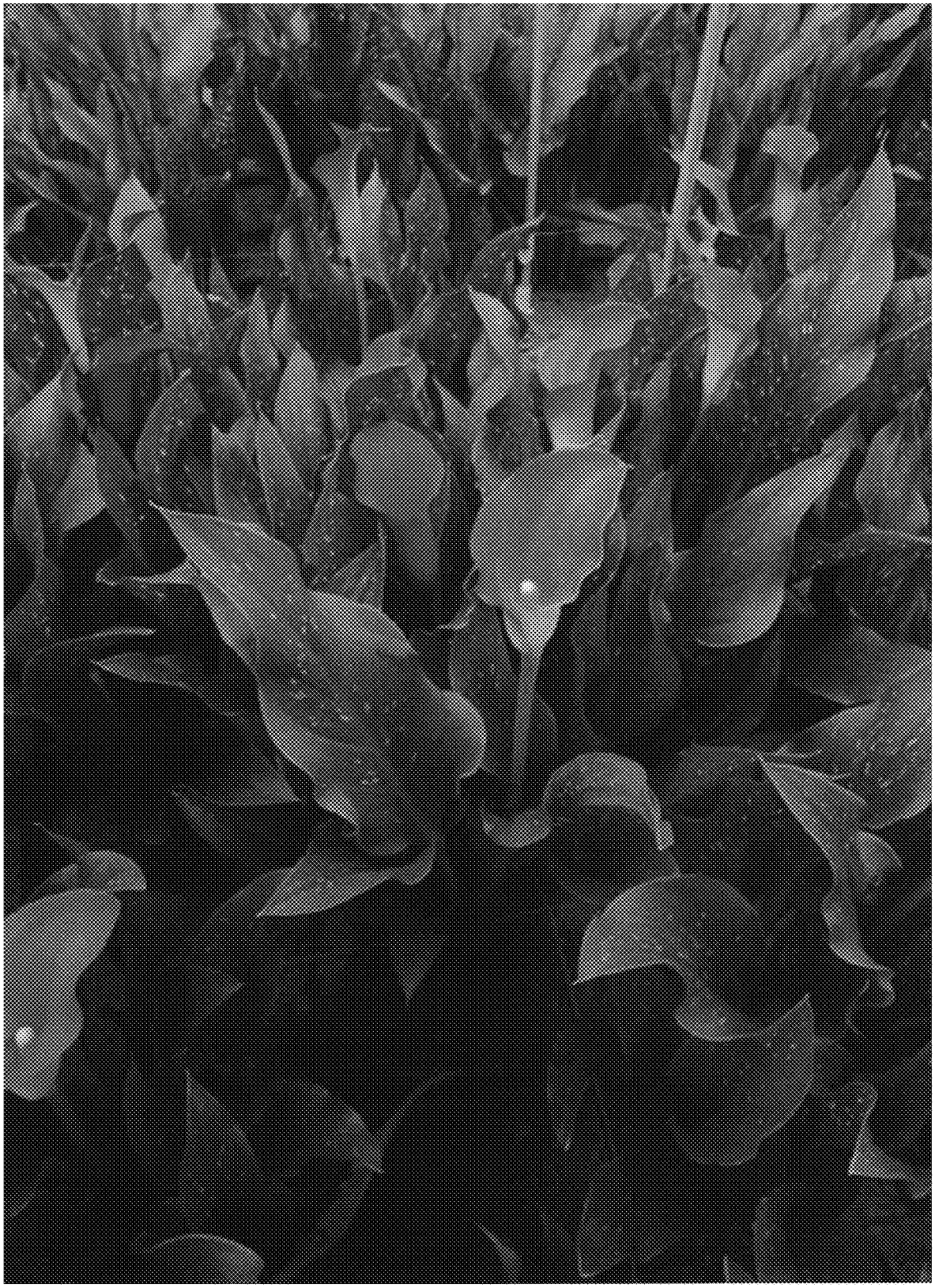
FIG. 1 illistrates a close-up perspective of multiple flowering plants of the new variety.
Figure 2:
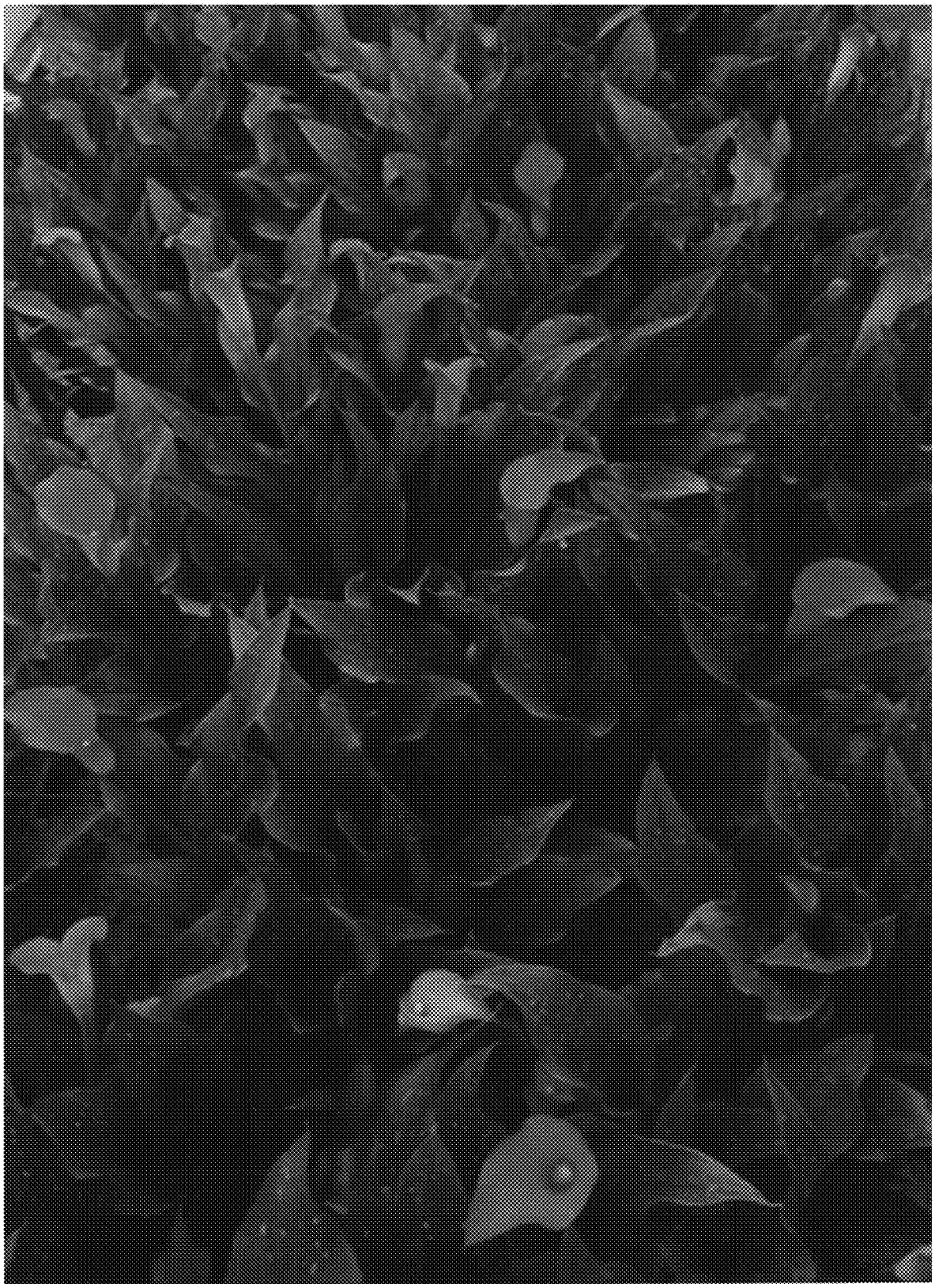
FIG. 2 illustrates multiple flowering plants of the new variety.

Type: Deciduous.

*Size.*—Height of the leaf canopy above the soil: 27-33 cm. Height of top of inflorescences above the soil: 40-48 cm. Diameter: 40-47 cm.

*Form.*—Semi-spreading.

*Number of inflorescences per tuber.*—Size approximately 20 cm in diameter: 7-10 inflorescences.

*Branches.*—Number: Average. Color: Yellow-Green Group RHS 144A to 144B. Young shoot color: Red-Purple Group RHS 64A to 64B.

Leaves:

*Size.*—Width: 8-10 cm, with the broadest part being slightly below the middle. Length: 24-27 cm.

*Number per plant.*—32-57.

*Leaf blade lobes.*—Absent.

*Shape.*—Lanceolate.

*Apex.*—Apiculate.

*Base.*—Attenuate.

*Margin.*—Entire; having a color of Yellow-Green Group RHS N144C to N144D.

*Color.*—Upper surface: Yellow-Green Group RHS 147B to 147C, with medium, linear Greyed-White Group RHS 156B to 156C maculations present. Lower surface: Yellow-Green Group RHS 146B to 146C, with medium, linear Greyed-White Group RHS 156D maculations present.

*Veins.*—Configuration: Pinnate. Color: Yellow-Green Group RHS N144D.

*Surface texture.*—Smooth (both surfaces).

*Petiole.*—Length: 29-36 cm. Diameter: 16-19 mm. Color: The base is Yellow-Green Group RHS 144B to 144C, the upper part is Yellow-Green Group RHS 144A to 144B.

*Roots.*—

*Color.*—White Group RHS 155C.

*Branching description.*—Fibrous root system. Several main roots emerge from the top of the tuber and form a small number of lateral roots.

Spathe:

*Size.*—Length (measured from opening to tip): 6-8 cm. Width: 4-5 cm. Height: 7-9 cm.

*Color.*—Throat spot: Absent. Upper surface: Red Group RHS 46B to 46C. Lower surface: Red Group RHS 45B to 45C.

*Vein color.*—Yellow-Green Group RHS 148C to 148D.

*Shape.*—Leaf-like.

*Apex.*—Caudate.

*Base.*—Attenuate.

*Margin.*—Entire, with a color of Red Group RHS 47A to 47B.

*Spadix.*—

*Shape.*—Cylinder.

*Size.*—Length: 30-35 mm. Diameter: 8-11 mm.

*Color.*—Yellow-Orange Group RHS 21A to 21B.

*Position relative to spathe.*—Upright.

*Peduncle.*—

*Size.*—Length: 37-50 cm. Diameter: 10-12 mm.

*Color.*—The upper part is Green Group RHS 143A to 143B, the lower part is Yellow-Green Group RHS 144B to 144C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: Between 480 and 600. Pollen amount: Scarce. Color: Between White Group RHS 155B and 155C.

*Anther.*—Shape: Round. Length: Less than 1 mm. Color: Yellow Group RHS 8B to 8C.

*Filament.*—Length: Less than 1 mm. Color: White Group RHS 155D.

*Pistils.*—Number: 15 to 30. Length beyond perianth: About 1 mm.

*Stigma.*—Shape: Round. Size: Less than 1 mm.

*Style.*—Length: Less than 1 mm. Color: Yellow Group RHS 8B to 8C.

*Ovaries.*—Texture: Smooth. Length: Between 1 to 10 mm. Width: Between 1 to 10 mm. Color: The top color is Orange Group RHS 25B to 25C, the bottom color is Green Group RHS 140B to 140C.

Seeds:

*Length.*—2.2-4.3 mm.

*Width.*—1.5-4.2 mm.

*Color.*—Yellow-Green Group RHS 153C to 153D.

*Amount.*—13 per inflorescence.

Disease resistance: No unusual susceptibility/resistance to diseases noticed to date.

*Pest resistance.*—No unusual susceptibility/resistance to pests noticed to date.

*Heat tolerance.*—No heat tolerance.

*Hardiness.*—Not tested to date.

*Flowering.*—In general, the time from indoor and outdoor planting to first flowering takes about eight weeks in The Netherlands.

*Lastingness.*—About two weeks on the plant.

*Fragrance.*—None.

I claim:

1. A new and distinct variety of calla lily plant named 'Dozancorv' as herein described and illustrated.

* * * * *